United States Patent [19]

Mezei

[11] Patent Number: 4,897,269

[45] Date of Patent: Jan. 30, 1990

[54] ADMINISTRATION OF DRUGS WITH MULTIPHASE LIPOSOMAL DELIVERY SYSTEM

[75] Inventor: Michael Mezei, Halifax, Canada

[73] Assignee: Mezei Associates Limited, Nova Scotia, Canada

[21] Appl. No.: 212,012

[22] Filed: Jun. 27, 1988

Related U.S. Application Data

[60] Division of Ser. No. 774,266, Sep. 10, 1985, Pat. No. 4,761,288, which is a continuation-in-part of Ser. No. 653,997, Sep. 24, 1984, abandoned.

[51] Int. Cl.$^4$ .................. A61K 9/66; A61K 37/22; B01J 13/02
[52] U.S. Cl. .................. 424/450; 264/4.1; 264/4.6; 428/402.2; 436/829; 514/78; 514/272; 514/880; 514/887; 514/944
[58] Field of Search .................. 428/402.2; 424/450; 436/829; 514/78, 272, 880

[56] References Cited

U.S. PATENT DOCUMENTS

| | | | |
|---|---|---|---|
| 3,645,911 | 2/1972 | van Besauw et al. | 264/4.6 |
| 3,804,776 | 4/1974 | Yazawa et al. | 427/213.3 |
| 4,016,100 | 4/1977 | Suzuki et al. | 264/4.3 |
| 4,048,310 | 9/1977 | Chen et al. | 514/873 X |
| 4,089,801 | 5/1978 | Schneider | 264/4.1 |
| 4,235,871 | 11/1980 | Papahadjopoulous et al. | 264/4.6 X |
| 4,342,826 | 8/1982 | Cole | 436/7 |
| 4,438,052 | 3/1984 | Weder et al. | 264/4.6 |
| 4,485,054 | 11/1984 | Mezei et al. | 264/4.6 |
| 4,532,089 | 7/1985 | MacDonald | 264/4.3 |
| 4,761,288 | 8/1988 | Mezei | 424/450 |

FOREIGN PATENT DOCUMENTS

| | | |
|---|---|---|
| 0084898 | 8/1983 | European Pat. Off. . |
| 85306641.3 | 4/1987 | . |
| 3335701A1 | 4/1984 | Fed. Rep. of Germany . |
| WO8503640 | 8/1985 | PCT Int'l Appl. . |
| 2050833A | 1/1981 | United Kingdom . |

OTHER PUBLICATIONS

Bangham et al., Methods in Membrane Biology, 6 (London 1974).
Bangham et al., Chem. Phys. Lipids 1:266 (1967).
Cecil-"Textbook of Medicine", vol. 1 (1982), pp. 1276-1278.
Chemical Abstracts, vol. 97, No. 22 (1982), Abstract No. 188156k.
Theoharides, "Liposomes as Carriers of Biologically Active Molecules", *Folia Bioch. et Biol. Graeca*, Special Issue, vol. XIV, pp. 11-21 (1978).
Mezei et al., Life Sciences, vol. 26, pp. 1473-1477 (1980).
Mezei, "Liposomes-A Selective Drug Delivery System for the Topical Route of Administration: Gel Dosage Form", *J. Pharm. Pharmacol.*, 1982, 34:473-474.

*Primary Examiner*—Richard D. Lovering
*Attorney, Agent, or Firm*—Banner, Birch, McKie and Beckett

[57] ABSTRACT

A method for administering a slightly water soluble biologically active compound by topically applying a pharmaceutical composition containing:
(a) lipid vesicles with a biologically active compound captured therein;
(b) a saturated solution of the biologically active compound; and
(c) the biologically active compound in solid form.

Optionally this composition is dispersed in a hydrocolloid gel.

6 Claims, No Drawings

ADMINISTRATION OF DRUGS WITH MULTIPHASE LIPOSOMAL DELIVERY SYSTEM

This application is a division, of application Ser. No. 774,266, filed September 10, 1985, now U.S. Pat. No. 4,761,288, which in turn was a continuation-in-part of application Ser. No. 653,997, filed September 24, 1984, now abandoned.

BACKGROUND OF THE INVENTION

The present invention relates to a novel drug delivery system. More particularly, the present invention relates to a product in which a biologically active material is present in a multiphase system, i.e., (a) captured in multilamellar lipid vesicles (MLV); (b) dissolved in the solvent components of the system; and (c) in a solid crystalline or amorphous state.

Liposomes are lipid vesicles composed of membrane-like lipid layers surrounding aqueous compartments. Liposomes are widely used to encapsulate biologically active materials for a variety of purposes, but particularly they are used as drug carriers. Depending on the number of lipid layers, size, surface charge, lipid composition and methods of preparation various types of liposomes have been utilized.

Multilamellar lipid vesicles (MLV) were first described by Bangham, et al., (J. Mol. Biol. 13:238:252, 1965). A wide variety of phospholipids form MLV on hydration. MLV are composed of a number of bimolecular lamellae interspersed with an aqueous medium. The lipids or lipophilic substances are dissolved in an organic solvent. The solvent is removed under vacuum by rotary evaporation. The lipid residue forms a film on the wall of the container. An aqueous solution generally containing electrolytes and/or hydrophilic biologically active materials are added to the film. Agitation produces larger multilamellar vesicles. Small multilamellar vesicles can be prepared by sonication or sequential filtration through filters with decreasing pore size. Small unilamellar vesicles can be prepared by more extensive sonication. An improved method of encapsulating biologically active materials in multilamellar lipid vesicles is described in U.S. Pat. No. 4,485,054.

Unilamellar vesicles consist of a single spherical lipid bilayer entrapping aqueous solution. According to their size they are referred to as small unilamellar vesicles (SUV) with a diameter of 200 to 500 Å; and large unilamellar vesicles (LUV) with a diameter of 1000 to 10,000Å. The small lipid vesicles are restricted in terms of the aqueous space for encapsulation, and thus they have a very low encapsulation efficiency for water soluble biologically active components. The large unilamellar vesicles, on the other hand, encapsulate a high percentage of the initial aqueous phase and thus they can have a high encapsulation efficiency. Several techniques to make unilamellar vesicles have been reported. The sonication of an aqueous dispersion of phospholipid results in microvesicles (SUV) consisting of bilayer or phospholipid surrounding an aqueous space (Papahadjopoulos and Miller, Biochem. Biophys. Acta., 135: 624–238, 1968). In another technique (U.S. Pat. No. 4,089,801) a mixture of a lipid, an aqueous solution of the material to be encapsulated, and a liquid which is insoluble in water, is subjected to ultrasonication, whereby liposome precursors (aqueous globules enclosed in a monomolecular lipid layer), are formed. The lipid vesicles are then prepared by combining the first dispersion of liposome precursors with a second aqueous medium containing amphiphilic compounds, and then subjecting the mixture to centrifugation, whereby the globules are forced through the monomolecular lipid layer and forming the bimolecular lipid layer characteristic of liposomes.

Alternate methods for the preparation of small unilamellar vesicles that avoid the need of sonication are the ethanol injection technique (S. Batzri and E. D. Korn, Biochem. Biophys. Acta. 298: 1015–1019, 1973) and the ether injection technique (D. Deamer and A. D. Bangham, Biochem. Biophys. Acta. 443: 629–634, 1976). In these processes, the organic solution of lipids is rapidly injected into a buffer solution where it spontaneously forms liposomes—of the unilamellar type. The injection method is simple, rapid and gentle. However, it results in a relatively dilute preparation of liposomes and it provides low encapsulation efficiency. Another technique for making unilamellar vesicles is the so called detergent removal method (H. G. Weder and O. Zumbuehl, in "Liposome Technology" ed. G. Gregoriadis, CRC Press Inc., Boca Raton, Florida, Vol. I, Ch. 7, pg 79–107, 1984). In this process the lipids and additives are solubilized with detergents by agitation or sonication yielding defined micelles. The detergents are then removed by dialysis.

Multilamellar vesicles can be reduced both in size and in number of lamellae by extrusion through a small orifice under pressure, e.g., in a French press. The French press (Y. Barenholz; S. Amselem and D. Lichtenberg, FEBS Lett. 99: 210–214, 1979), extrusion is done at pressures of 20,000 lbs/in at low temperature. This is a simple, reproducible, nondestruction technique with relatively high encapsulation efficiency, however it requires multilamellar liposomes as a starting point, that could be altered to oligo- or unilamellar vesicles. Large unilamellar lipid vesicles (LUV) can be prepared by the reverse phase evaporation technique (U.S. Pat. No. 4,235,871, Papahadjopoulos). This technique consists of forming a water-in-oil emulsion of (a) the lipids in an organic solvent and (b) the substances to be encapsulated in an aqueous buffer solution. Removal of the organic solvent under reduced pressure produces a mixture which can then be converted to the lipid vesicles by agitation or by dispersion in an aqueous media.

U.S. Pat. No. 4,016,100, Suzuki, et al., describes still another method of entrapping certain biologically active materials in unilamellar lipid vesicles by freezing an aqueous phospholipid dispersion of the biologically active materials and lipids. All the above liposomes, made prior to 1983, can be classified either as multilamellar or unilamallar lipid vesicles. A newer type of liposomes is referred to as multivesicular liposomes (S. Kim, M. S. Turker, E. Y. Chi, S. Sela and G. M. Martin, Biochim. Biophys. Acta 728; 339–348, 1983). The multivesicular liposomes are spherical in shape and contain internal granular structures. A lipid bilayer forms the outermost membrane and the internal space is divided up into small compartments by bilayer septrum. This type of liposomes required the following composition: an amphiphatic lipid with net neutral charge, one with negative charge, cholesterol and a triacylglycerol. The aqueous phase containing the material to be encapsulated is added to the lipid phase which is dissolved in chloroform and diethyl ether, and a lipid-in-water emulsion is prepared as the first step in preparing multivesicular liposomes. Then a sucrose solution is shaken with the water-in-lipid emulsion; when the organic solvents are evaporated liposomes with multiple compartments are formed.

For a comprehensive review of types of liposome and methods for preparing them refer to a recent publication "Liposome Technology" Ed. by G. Gregoriadis, CRC Press Inc., Boca Raton, Florida, Vol. I, II, & III 1984.

Solutions are one of the oldest type of pharmaceutical dosage forms or drug delivery systems. A true solution is defined as a mixture of two or more components that form a homogeneous molecular dispersion, i.e., a one phase system. According to the United States Pharmacopeia, Twentieth Revision (USP XX, page 1027), solutions are liquid preparations that contain one or more soluble chemical substances usually dissolved in water. Further, solutions are used for the specific therapeutic effect of the solute, either internally or externally. Id.

Suspensions are preparations of finely divided, undissolved drugs dispersed in liquid vehicles (USP XX page 1030). In this sense a suspension is a heterogenous, two-phase system. Suspensions have been used as drug delivery systems for centuries, for providing an insoluble bioactive ingredient for oral, parenteral and for the topical route of administration. In the present multicomponent, multiphase liposomal system the biologically active substance is present in the solid form dispersed in the aqueous medium both inside and outside the lipid vesicles.

Hydrogels can be any one of a wide variety of synthetic and natural hydrophilic polymers. They are used in pharmaceutical dosage formulation for various purposes, i.e., as viscosity inducing agents for suspensions and ophthalmic solutions; as protective colloids to stabilize emulsions and suspensions; as vehicles for topically applied dosage forms; as controlled-release drug delivery systems (J. D. Andrade (ed) "Hydrogels" for Medical and Related Applications" ACS Symposium, Series Nol. 31 ACS Washington, D.C., 1976). A gel is generally a semisolid system of at least two constituents, consisting of a condensed mass enclosing and interpenetrated by a liquid. The gel mass may consist of flocculles of small particles or macromolecules existing as twisted, intermingled, matted strands. The polymer units are often bound together by electrostatic, hydrogen and van der Waal forces. Gels containing water are called hydrogels, those containing organic liquid are called organogels.

The hydrophilic polymers in aqueous media exhibit "pseudoplastic flow" due to the effect of intermolecular entanglements and the binding of water molecules. When the long randomly coiled polymer chain moves, their solvation layer (water of hydration) are dragged along which increases the resistance to flow, or the viscosity of the solution. This property is often utilized in pharmaceutical formulation to increase the viscosity of the preparation. Recently the hydrogels have been disclosed as useful for a controlled drug delivery system (S. W. Kim, Pharmacy International 4: 90–91 (1983)).

PRIOR ART

A large number of liposomal preparations are known, as described above. A method for preparing liposomal preparations using contact masses such as glass beads to increase the surface area for liposome formation is described in U.S. Pat. No. 4,485,054. Several publications disclose the use of glass beads and the like to accelerate dispersion during the addition of the aqueous phase. See, e.g., U.S. Pat. No. 4,342,826; UK patent application No. 2,050,833; A. D. Bangham, et al., Methods in Membrane Biology 6 (London 1974); and A. D. Bangham, et al., Chem. Phys. Lipids 1:266 (1967).

SUMMARY OF THE INVENTION

The present invention particularly provides:
a pharmaceutical composition comprising:
(a) multilamellar lipid vesicles with a slightly water soluble biologically active compound captured therein;
(b) a saturated solution of the biologically active compound; and
(c) the biologically active compound in solid form.

The present invention further provides:
(1) the composition described above wherein the vesicles, the solution, and the solid form of the biologically active compound are dispersed in hydrocolloidal gel; and
(2) a method for preparing this latter composition comprising
    (a) providing a vessel partially filled with inert, solid contact masses;
    (b) providing a lipid component and the biologically active material dissolved in a suitable organic solvent within the vessel;
    (c) removing the organic solvent by evaporation so as to form a thin lipid film on the inner wall of the vessel and on the surfaces of the contact masses;
    (d) thereafter adding an aqueous liquid solution containing the biologically active material and possibly electrolytes and hydrocolloids to the vessel, and agitating the vessel to form an aqueous dispersion of lipid, gel and bioactive substances; and
    (e) allowing the dispersion to stand essentially undisturbed for a time until the formation and dispersion of the multilamellar lipid vesicles and the hydrogel is completed.

The present invention further provides:
a method for administration of slightly water soluble biologically active compounds comprising topically applying a composition described above.

Alternatively, where the biologically active material has a melting point low enough to be fused together with the lipid components without any chemical decomposition (typically less than 100° C.) and the biologically active ingredient(s) in powder form and placed in the vessel containing the solid contact masses and fused together by rotating or shaking the vessel.

During the above procedures, a person having experience in the art of making liposomes can easily realize, that optimal results can be achieved, if various temperatures are utilized, depending on the transition temperature of the lipid component(s) and depending on the nature of the hydrogels, the efficiency of encapsulation can be favorably affected by selection of the appropriate types of lipids, the shape and size of the vessel in which the procedures are carried out, the amount and size of solid contact masses, the degree of vacuum during evaporation and the agitation and the temperature during hydration of the lipid film. A thin, even film is desired for optimal results.

Generally, dipalmitoyl phosphatidyl choline, pear shaped flasks, mild heating, (up to about 60° C.) and mild vacuum are preferred.

The present invention thus provides a liposomal product which contains a biologically active material in a higher concentration than its water and/or lipid solubility. The active material is dispersed in the product in (a) liposome encapsulated form (b) in super-saturated solution form and (c) in solid form. Further objectives of this invention are: (a) to provide a process that ensures maximum encapsulation of the biologically active material in the lipid vesicles; (b) to efficiently accommodate both lipophilic and hydrophilic substances; and (c) to provide a process of preparation which is applicable for large scale production.

A product composed of the multicomponent system of this invention is suitable for various routes of drug administration, i.e., oral, rectal, parenteral and particularly local administration to the skin, eye and mucous membranes. This multicomponent system, in which the active ingredient is present in two states, i.e., in solution and in solid form within and outside the lipid vesicles provides a unique biopharmaceutical system, where the absorption and disposition of the biologically active material can be optimized. It is especially useful for local activity because of the different rates of absorption, distribution (clearance) and metabolism, due to its various states, (i.e., in the "free" form in solution, as solid particles, in the liposome-encapsulated form, and as dissolved molecules and particles).

These and other objectives are achieved by utilizing the method for preparing multilamellar lipid vesicles described in U.S. Pat. No. 4,485,054, and is expressly incorporated herein by reference, to formulate a biologically active ingredient in a concentration above its water and lipid solubility.

The process is characterized by the following steps:

(a) providing a vessel partially filled with inert, solid contact masses;

(b) providing a lipid component and the biologically active material dissolved in a suitable organic solvent within the vessel;

(c) removing the organic solvent by evaporation so as to form a thin lipid film on the inner wall of the vessel and on the surfaces of the contact masses;

(d) thereafter adding an aqueous liquid containing the biologically active material and/or other substances to the vessel and agitating the vessel to form an aqueous dispersion of lipid and bioactive substance; and (e) allowing the dispersion to stand essentially undisturbed for a time until the formation and dispersion of the multilamellar lipid vesicles is completed.

As noted above, the lipid film can be formed without using organic solvents if the ingredients (lipids and biologically active materials) have a melting point low enough to be fused together with the lipid components without causing thermodecomposition.

If desired the size of the lipid vesicles and solid particles can be reduced by ultrasonication. Dispersion of the lipid vesicles and the bioactive material (including the gel) can be further improved by putting the product through a homogenizer.

To manufacture the liposomal preparations of the present invention on a larger scale. The procedure described above (and in U.S. Pat. No. 4,485,054) is modified by replacing the wrist action shaker with a gyro shaker and using an oven to provide the appropriate temperature environment rather than a water bath. Equipment employing a container and a shaker with gyro action could be used.

In the present invention the biologically active material is dissolved, i.e., present in a molecular state in both the aqueous media and in the lipid media. Its aqueous solution is present both within and outside the lipid vesicles. Since the present invention contains the biologically active material also in the solid form, the solution phase should be in a saturated state.

As used in the specification and claims, the terms (a) "biologically active material", "biologically active substance" or "bioactive" ingredient mean a compound or composition which, when present in an effective amount, produces an effect in living cells or organisms. Examples of biologically active compounds used in this invention include dermatological agents, (e.g., triamcinolone acetonide, retinoic acid); antibacterial agents (e.g., ampicillin); antifungal agents (e.g., econazole base, econazole nitrate, amphotericine B); anti-convulsants (e.g., diphenylhydantoin); antihypertensive agents (e.g., minoxidil); anticancer agents (e.g., methotrexate); immunomodulators (e.g., lipophillic derivatives of muramyl dipeptide), antiviral agents (acyclovir, interferons); non-steroidal anti-inflammatory agents (e.g., ibuprofen); and the like. By "slightly water soluble" is a solubility in water which is too low for the biologically active compound to be practically used in conventional aqueous solution formulations, i.e., the water solubility compared to the potency of the compound is too low for an effective dose to be practically administered in aqueous solution form or in other types of liposomal forms. Examples of such slightly soluble biologically active compounds are those described above.

"Hydrogel", "hydrocolloid" or "gel" means any chemical substance which exhibits the ability to swell in water, retaining a significant amount of water within its structure; it could be inorganic, e.g., bentonite or organic, e.g., methylcellulose; single or polymer compound. Any of the known lipids and lipid-like substances can be used in the present invention, both from natural or synthetic sources, such as ceramides, lecithins, phosphatidyl ethanolamines, phosphatidyl serines, cardiolipins, trilinoleins, phophatidic acid, and like compounds.

The present invention may be used as a vehicle for drug delivery for both human and veterinary purposes. By "drug" is meant any biologically active compound which is useful for human or veterinary purposes and is capable of being captured by the vesicles of this invention.

Thus, drugs which are employed in the present invention are any slightly water soluble drug capable of being captured by the lipid vesicles in some way. "Captured" includes entrapment within the enclosed lipid bilayer (either by fusing smaller vesicles around the drug or by transmission through the membrane or forming the lipid vesicles within the solution containing the drug), or (for lipophilic or ampophilic drugs) incorporation into, or binding them to, the lipid membrane itself. These drugs may be of varying degrees of lipophilicity, and their use in the present invention would be obvious to a pharmaceutical formulator skilled in the art of lipid chemistry when the properties of these vesicles are described.

Advantages of this multicomponent liposomal system are:

(a) Biologically active ingredients can be incorporated into this liposomal system in a concentration higher than their water or lipid solubility.

Consequently this system is particularly suitable for compounds with low lipid or water solubility where purely liposomal preparations can contain the ingredient only in low concentration, which may prevent proper dosing for activity of the ingredient in solution or other previously known liposomal forms.

(b) The bioactive ingredients are present in this system (i) in solution form possibly in a supersaturated state, either encapsulated in the lipid vesicle, or outside the lipid vesicle in both the aqueous and in the lipid phase; and (ii) in solid state, crystalline or in amorphous form both within or outside of the lipid vesicles.

Consequently the biopharmaceutical fate of the bioactive material will be different according to its state, i.e., the rate of absorption and in vivo disposition of the liposome-encapsulated, and the "free" solution, and the solid form of the ingredient will be different. It is anticipated that this difference will provide a sustained-prolonged action.

(c) The activity of the bioactive ingredients may be localized at or near the site of application, i.e., skin, eye and mucocutaneous membranes (lung, nose, and gastrointestinal tract, and vagina). The large multilamellar lipid vesicles penetrate these organs, but, because of their size, they are not taken up by the blood circulation. The lipid vesicles may also act within the organ, as a slow-release vehicle. The prolonged release and the reduced clearance rate leads to an accummulation of the bioactive ingredient at or near the site of application, which results in an intensification and also in prolongation of the local action, with a reduction in systemic action. The "free" form also penetrates into these organs at a higher rate, because of the presence of liposomes results in an occlusive effect. The "free" form of the bioactive ingredient can also be bound to the lipid vesicles or "dragged along" with the liposomes into the tissue.

The hydrogels, besides influencing the structure and inter-relation of the lipid vesicles, are particularly useful for topical application because of their effect on the viscosity and adhesive properties of the final product. Certain hydrogels also directly affect the absorbing biological membranes, especially the muco-cutaneous membranes.

The bioactive ingredient is dissolved in the aqueous solution at a saturation level. The bioactive material is also present in the lipid film in a concentration higher than its lipid solubility. The liposome formation is taking place at higher than room temperature, therefore, at the completion of the product, the bioactive ingredient will be present in solution in both the aqueous and lipid phase in a saturated state and also in crystalline or amorphous solid state. No attempt is made to prepare and separate the liposomal fraction. Instead the system is intentionally made heterogeneous, where the bioactive material is dispersed in solution and in solid form both within and outside the lipid vesicles, and the lipid vesicles are dispersed in an aqueous media.

The present invention differs from previously known liposomal compositions in that the product formed contains the biologically active material in solid and molecular (dissolved) state in both "liposome-encapsulated" and in "free" form.

DESCRIPTION OF THE PREFERRED EMBODIMENTS

The present invention is seen more fully by the Examples given below.

EXAMPLE 1

| Formula | | |
|---|---|---|
| (i) | DL alpha dipalmitoyl | |
| | phosphatidylcholine (DPPC) | 400 mg |
| | Cholesterol | 200 mg |
| | Minoxidil | 100 mg |
| (ii) | Minoxidil | 20 mg |
| | Ethanol (95%) | 1 ml |
| | Propylene glycol | 0.7 ml |
| | Calcium chloride (8 mM) | |
| | solution | 8.3 ml |

(i) Components of (i) DPPC, cholesterol and minoxidil were co-dissolved in 100 ml of chlorform-methanol solvent (2:1) in a 500 ml pear-shaped flask. The solvent was evaporated under vacuum in a rotary evaporator; the lipid and minoxidil residue formed a thin film on the wall of the pear-shaped flask.

(ii) Separately 20 mg minoxidil was dissolved in 0.7 ml propylene glycol and 1 ml ethanol in a 50 ml Erlenmeyer flask at 40°–50° C.; 8.3 ml CaCl$_2$ solution was added and the temperature of this solution was brought up to 55°–60° C.

The pear-shaped flask containing the lipid-minoxidil solid film still under vacuum was also brought up to 55°–60° C. The aqueous solution (ii) was added to the lipid-minoxidil film and shaken with the aid of a wrist shaker for 30 minutes immersed in a water bath set at 60° C. The resultant liposomal suspension was allowed to stand for one hour at room temperature.

One droplet of this preparation was examined microscopically under polarized light with 640×magnification. Spherical shaped liposomes of various sizes (between 1μ to 15μ diameters) were observed along with minoxidil crystals.

EXAMPLE 2

| Formula | | |
|---|---|---|
| (i) | DL alpha dipalmitoyl | |
| | phosphatidylcholine (DPPC) | 400 mg |
| | Cholesterol | 200 mg |
| | Minoxidil | 100 mg |
| (ii) | Minoxidil | 20 mg |
| | Ethanol (95%) | 1 ml |
| | Propylene glycol | 0.7 ml |
| | Calcium chloride (8 mM) | |
| | solution | 8.7 ml |
| (iii) | Methylcellulose 1500 cps | 10 mg |

(i) Components of (i) DPPC, cholesterol and minoxidil were co-dissolved in 100 ml of chloroform-methanol solvent (2:1) in a 500 ml pear-shaped flask. The solvent was evaporated under vacuum in a rotary evaporator; the lipid and minoxidil residue formed a thin film on the wall of the pear-shaped flask. (ii) Separately 20 mg of minoxidil in 1 ml of ethanol were placed in an Erlenmeyer flask at 40°–50° C.; 8.3 ml CaCl$_2$ solution was added and the temperature of this solution was brought up to 55°–60° C.

The pear-shaped flask containing the lipid-minoxidil solid film still under vacuum was also brought up to 55°–60° C. Then the aqueous solution (ii) and the 10 mg Methylcellulose powder (iii) were added to the lipid-minoxidil film and shaken with the aid of a wrist shaker for 30 minutes immersed in a water bath set to 60° C. The flask was then placed in an ice-bath (approx. 4° C.) and shaken there for 10 minutes. The resultant liposomal suspension was allowed to stand for one hour at room temperature.

One droplet of this preparation was examined microscopically under polarized light with 640×magnification. Spherical and tubular shaped liposomes of various sizes (between 1μ to 15μ diameters) were observed along with minoxidil micro crystals. Most of the liposomes were closely associated with each other forming unusual conglomerates of the lipid vesicles interspaced with the hydrocolloid (methylcellulose) bridges.

EXAMPLE 3

| Formula | | |
|---|---|---|
| (i) | DL alpha dipalmitoyl phosphatidylcholine (DPPC) | 400 mg |
| | Cholesterol | 100 mg |
| | Minoxidil | 100 mg |
| (ii) | Minoxidil | 20 mg |
| | Sodium Carboxymethylcellulose | 10 mg |
| | Ethanol (95%) | 1 ml |
| | Propylene glycol | 0.7 ml |
| (iii) | Calcium chloride (8 mM) solution | 8.3 ml |

(i) Components of (i) DPPC, cholesterol and minoxidil were co-dissolved in 100 ml of chloroform-methanol solvent (2:1) in a 500 ml pear-shaped flask. The solvent was evaporated under vacuum in a rotary evaporator; the lipid and minoxidil residue formed a thin film on the wall of the pear-shaped flask. (ii) Separately 20 mg minoxidil was dissolved in 0.7 ml propylene glycol and 1 ml ethanol. This solution is gradually added to 10 mg sodium carboxymethylcellulose to prewet the hydrocolloid. $CaCl_2$ solution (8.3 ml) is heated up to 55°–60° C. and added to the flask containing the lipid-minoxidil film. Within 1–2 seconds the sodium carboxymethylcellulose suspension was added to the same flask which was immersed in a water bath set to 60° C. Then the flask was shaken with the aid of a wrist shaker for 30 minutes immersed in a water bath set to 60° C. The resultant liposomal suspension was allowed to stand for one hour at room temperature.

One droplet of this preparation was examined microscopically under polarized light with 640×magnification. Spherical and tubular shaped liposomes of various sizes (between 1μ to 15μ diameters) were observed along with a few micro crystals. Most of the liposomes were closely associated with each other forming unusual conglomerates of the lipid vesicles interspaced with the hydrocolloid (sodium carboxy methylcellulose) bridges.

EXAMPLE 4

In a manner similar to the preceding examples several other compositions were prepared and tested, including (a) varying the concentrations of methylcellulose (0.1%–1%), and minoxidil (3%);

(b) using purified soybean or egg lecithin in place of the DPPC;

(c) using other hydrocolloids (e.g., Veegum, colloidal silica, xanthan, tragacanth);

(d) including preservative or antioxidant agents (e.g., benzoic acid, methyl and propyl paraben, BHA, tocopherol, benzyl alcohol);

(e) varying the proportion of DPPC, or other type of lecithins, and cholesterol; and (f) using other slightly soluble compounds in place of the minoxidil, e.g., econazole base, econazole nitrate, progesterone, β-estradiol, testosterone and the others described above.

Glass beads (40–60 beads with 5 mm diameter) usually were placed in the pear-shaped flask before the evaporation of the organic solvent. The products prepared in the presence of glass beads always had a better quality in comparison to those prepared without glass beads; i.e., they contained a higher number of liposomes and a smaller number of minoxidil crystals. Another advantage of using the glass beads is that the minoxidil crystal size was greatly reduced and the intermingling of the hydrocolloids and lipid vesicles was more noticeable. The major advantage of using the glass beads or any solid contact masses is of course the possibility of large, industrial scale production.

EXAMPLE 5

In this example minoxidil as a model for a slightly soluble biologically active material is incorporated in the multicomponent (heterogeneous) liposomal system of Examples 1 and 2. This compound was selected, because of its physicochemical properties, because of its solubility properties (very slightly soluble in aqueous or in lipid media), it is not a good candidate for liposomal encapsulation. This compound is an oral antihypertensive agent (the active ingredient of LONITEN Tablets), and is useful topically to grow hair (See U.S. Pat. No. 4,139,619). The known methods to encapsulate minoxidil in uni- and multilamellar liposomes resulted in liposomal preparations containing no more than 0.2–0.4% minoxidil (see Table I). The liposomal encapsulation of the bioactive ingredient is always limited by its solubility, i.e., one cannot make the liposomal preparation more concentrated, than the solubility of the bioactive ingredient in the liposomal media. Minoxidil solubility in deionized water is 2.4 mg/ml (0.24%), and in organic solvents (e.g., chloroform, acetone, ethyl acetate, benzene, diethyl ether, 2-propanol, etc.) minoxidil solubility is less than 1 mg/ml (0.1%).

According to the present invention multicomponent liposomal systems that contain 1.2%, 2%, and 3% minoxidil were prepared. It is possible to increase the minoxidil concentration even higher. The total amount of minoxidil was not present within the lipid vesicles; some portion of the minoxidil was outside the lipid vesicle in solution and in solid form, but as a drug delivery system this is advantageous for topical application, for localizing the bioactive ingredient (i.e., minoxidil) at or within the organ to which the composition is applied. Results of animal experiments for drug disposition studies confirm this. The test preparations contained 1.2%, 2%, and 3% minoxidil in the multicomponent liposomal drug delivery system. Two control preparations were used, containing corresponding concentrations of minoxidil (i.e., 1.2%, 2%, and 3%) in a solution form. A 2% minoxidil suspension, containing the identical lipid components in a nonliposomal form, was also prepared for control purposes.

The hair of the dorsal area of albino guinea pigs (300–500 g) was clipped off and an area of 3×3 cm was marked. Five groups of guinea pigs were used; the first group was treated with multiphase liposomal minoxidil 1.2%, the second group with 1.2% minoxidil solution, the third with 1.2% minoxidil in a multiphase liposome containing 0.1% methyl cellulose, the fourth group with 3% minoxidil solution, and the fifth group with 3% minoxidil in a multiphase liposome containing 0.1% methylcellulose. A 0.1 ml dose was applied in a twice a day dosage schedule. A dose of 0.05 ml twice a day was used for the 2% minoxidil preparations.

The guinea pigs were treated at t=0, 8, 24, 32, 48, 56, and 72 hours, for a total of seven doses. The drug disposition was determined four hours after the last dose was applied.

The results are presented in Tables II and III.

The multicomponent liposomal dosage form produced higher concentration of minoxidil in all skin tissues compared to the conventional solution form. There was no significant difference between the drug concentrations measured in the internal organs of guinea pigs treated with minoxidil in liposomal or in solution form.

EXAMPLE 6

| (i) | L α dipalmitoyl phosphatidylcholine | 400 mg |
| --- | --- | --- |
|  | Cholesterol | 100 mg |
|  | Econazole base | 100 mg |
| (ii) | Benzoic acid | 20 mg |
|  | Butylated hydroxyanisole | 0.5 mg |
|  | Ethanol | 1 ml |
|  | CaCl$_2$ solution, 8 mM | 9 ml |
| (iii) | Methylcellulose 1500 | 10 mg |

In this example the fine powder form of the lipid components and of the econazole base was placed in a 500 ml pear-shaped flask along with 50–60 glass beads (5 mm diameter). The flask was then placed in a water bath set at 80° C. and rotated gently, with an approximate 60–80 RPM for 15 minutes. The lipids and drug content of the flask liquefied and fused together decreasing the temperature to 60° C. while maintaining rotation yielded a smooth dry film of the components which was formed on the surface of the glass beads and on the wall of the flask.

In a separate flask (50 ml Erlenmeyer flask) benzoic acid and butylated hydroxyanisole was dissolved in 1 ml ethanol and 9 ml CaCl$_2$ solution was added gradually at 40°. Then both flasks were placed in a waterbath at 60° and within 2–3 minutes the aqueous solution (ii) and the methylcellulose (iii) was added to the dry lipid and econazole base. The flask was shaken with the aid of wrist shaker for 20 minutes at 55°–60° temperature. The resultant liposomal suspension was shaken in a ice-bath (4°) for 10 minutes, then it was allowed to stand for one hour at room temperature.

This example demonstrates a means of preparing liposomes without using any organic solvent, thereby eliminating the need of the experimental steps of dissolving the lipid components and evaporating the organic solvent. The melting point of econazole base was low enough (80° C.) to fuse together with the lipid component. With aid of the glass beads (any other solid contact masses will also work), a thin film of the solid state of the lipids and biologically active materials was prepared. The lipids were then hydrated with an aqueous solution. One droplet of this preparation was examined microscopically under polarized light with 640× magnification. Spherical and tubular shaped liposomes (of various sizes (between 1–7μ diameter) were observed with econazole crystals. Most of the liposomes were conglomerated, the methylcellulose fibres were intermingled with the individual and aggregated lipid vesicles.

EXAMPLE 7

| (i) | L-α-dipalmitoyl phosphatidylcholine | 400 mg |
| --- | --- | --- |
|  | Cholesterol | 200 mg |
|  | Econazole nitrate | 100 mg |
| (ii) | Benzoic acid | 20 mg |
|  | Butylated hydroxyanisole | 0.5 mg |
|  | Ethanol | 1 ml |
|  | CaCl$_2$ Solution, 8 mM | 9 ml |

L-α-Dipalmitoyl phosphatidylcholine, cholesterol, and econazole nitrate were dissolved in chloroform: methanol (2:1) in a 500 ml pear-shaped flask. 50–60 Glass beads with 0.5 mm diameter were placed in the flask. The solvent was evaporated under vacuum in a rotary evaporator until a smooth, dry lipid film was observed on the glass beads and on the sides of the flask (i).

Benzoic acid and the butylated hydroxyanisole were dissolved in ethanol and the CaCl$_2$ solution was gradually added at 40° (ii). Both flasks (i) and (ii) were placed in a waterbath set to 60° and within 5 minutes the CaCl$_2$ solution (ii) was added to the dry film of the lipids and econazole nitrate (i). The flask was vigorously shaken for 30 minutes and then allowed to stand at room temperature for one hour.

One droplet of this preparation was examined microscopically under polarized light. Spherical and tubular shaped liposomes of various sizes between 1–9μ diameters) were observed with many econazole nitrate crystals. The size of these crystals were larger (approximately 10–20μ) than in the preparation described under Example 6. The lipid vesicles were not aggregated in this preparation.

EXAMPLE 8

| (i) | Vegetable lecithin (ethanol extract) | 800 mg |
| --- | --- | --- |
|  | Cholesterol | 200 mg |
|  | Econazole nitrate | 100 mg |
| (ii) | Benzoic acid | 20 mg |
|  | Butylated hydroxyanisole | 0.5 mg |
|  | Ethanol | 1 ml |
|  | CaCl$_2$ solution, 8 mM | 9 ml |

The components of (i) were dissolved in 10 ml chloroform: methanol (2:1) in a 500 ml pear-shaped flask. Glass beads (50–60 with 5 mm diameters) were added and the organic solvent was evaporated with the aid of a rotary evaporator. The residue of the lipids and econazole nitrate formed a thin film on the surface of the glass beads and on the wall of the pear shaped flask. The angle of the pear-shaped flask attached to the rotary evaporator was adjusted that the evaporating solvent had a maximum contact with the glass beads and the wall of the flask.

Benzoic acid and the butylated hydroxyanisole were dissolved in ethanol and the CaCl$_2$ solution was gradually added to this alcoholic solution. The content of both flasks was brought up to 60° in a water-bath. The aqueous solution added to the pear-shaped flask containing the thin film of the lipid and econazole nitrate residues. The flask was vigorously shaken at 60° for 30 minutes. The resultant liposomal suspension was allowed to stand for one hour at room temperature. Microscopic examination indicated that spherical and tubular shaped liposomes were formed (1–12μ diameters). Most of the liposomes were connected with each other, 4 to 6 lipid vesicles in one bundle. A large number of econazole nitrate crystals were observed under the polarized light.

EXAMPLE 9

Two preparations described above by Examples 7 and 8 were tested against a control preparation (PevarylR) containing the same concentration (1%) econanozole nitrate but in a cream vehicle base. The purpose of these tests were to study the drug disposition in guinea pigs after topical application of these products.

The hair of the dorsal area of albino guinea pigs (300–500 g) was clipped off and an area of 3×3 cm was marked. A 0.1 ml dose was applied in a "twice a day" dosage schedule, i.e.: t=0, 8, 24, 32, 48, 56, and 72 hours. Three groups of guinea pigs were used; one group was treated with the control preparation (PevarylR); the second and the third groups with the liposomal products described in Examples 7 and 8 respectively.

Ninety minutes after the last treatment the guinea pigs were killed under $CO_2$ atmosphere. Blood and other tissue samples were taken immediately. The samples were kept in deep freeze ($-16°$ C.) condition until processed for analysis. The skin samples were sliced horizontally with a Castroviejo Keratotome, set to 0.2 mm slice (the epidermis), then 0.5 mm slice (the dermis) and the remaining portion labelled as the subcutaneous tissue. The results are presented in Table IV.

From these results it could be concluded that the multicomponent dosage form produced higher concentration of econazole nitrate in all skin tissue than the cream form. The drug concentration measured in the internal organs of guinea pigs treated with econazole nitrate in the newly developed liposomal forms were usually lower than of those treated with the control, cream form.

The data also indicates that the multicomponent liposomal drug delivery system of the present invention is particularly useful for topical drug delivery and has a special advantage of accommodating slightly soluble biologically active substances in a concentration above than their lipid or water solubility.

EXAMPLE 10

Method for Large Scale Production of Liposomal Minoxidil Preparation

| | | Formula: Each 100 ml contains | |
|---|---|---|---|
| | | 4.0 g | Lecithin (Soy Phosphatide NC 95-H) |
| | | 2.0 g | Cholesterol USP |
| | | 2.0 g | Minoxidil Milled |
| | | 5.0 mg | Butylated Hydroxyanisole USP |
| | | *0.9 ml | Benzyl Alcohol NF |
| | | 10.0 ml | Ethanol (95%), USP |
| | | 7.0 ml | Propylene Glycol USP |
| (82.1)* | (82.0)** | 83.0 ml | 8 mM $CaCl_2$ solution |
| | ** | 1.0 ml | Tween 80 |

*Alternate Formula with preservative, benzyl alcohol
**Alternate Formula with surfactant, Tween 80
* & **If Tween 80 and/or benzoyl alcohol are used they displace an equivalent volume of $CaCl_2$ solution

Stock Solution

1. $CaCl_2$ (8 mM)

For each 1 liter volume prepared in a suitable volumetric flask, 1.176 g of Calcium Chloride dihydrate USP is first dissolved in purified water USP and then diluted to volume with purified water USP. This material may be used for up to one month after the date of preparation.

A. Step 1: Lipid-Minoxidil Film Coating (Batch size 500 ml)

To a 2 liter pear shaped flask attached to a rotary evaporator is added the following:

| Material | |
|---|---|
| Lecithin | 20 g |
| Cholesterol USP | 10 g |
| Minoxidil Milled | 8 g |
| Chloroform | 113 ml |
| Methyl Alcohol | 67 ml |
| 6 mm glass beads | 450 g |

The mixture is agitated at room temperature until fully dissolved.

Placing the evaporating flask on a Rotovapor at an angle so that none of the solution spills out of the neck, and so that rotation (approximately 80 rpm) provides gently continuous motion of the glass beads, the solvent is removed by heating the flask to $34°\pm2°$ C. and reducing the pressure to $100\pm50$ torr. The solvent is continued to be evaporated until visually the glass beads appear to be uniformly coated with an opaque layer of solids. If no uniform, thin film is formed, the procedure is repeated, i.e., the residue is dissolved in 200 ml $CHCl_3$: $CH_3OH$ (2:1) and the solvent is evaporated as above.

The solvent collection flask is emptied and the flask and contents are allowed to remain under vacuum for an additional 15 min for complete removal of any residual solvent. Note: beads may begin to stick to the sides of the flask. If during continued rotation the beads do not come off, the rotation is stopped and the sides of the flask are gently tapped until the beads are all dislodged. Rotation is then resumed. The beads should be freely rolling due to rotation.

Once the lipid minoxidil residue is dry of solvents, it may be stored at refrigerator temperature in a tightly closed container under a nitrogen atmosphere for up to 10 days.

B. Step 2 Hydration of Lipids (Liposome Formation)

For each 2 liter capacity flask plus glass beads coated in Step 1, the following solution is added, prepared as follows:

| Materials | |
|---|---|
| Minoxidil Milled | 2 g |
| Butylated Hydroxyanisole USP (BHA) | 25 mg |
| Ethanol USP (95%) | 50 ml |
| Propylene Glycol USP | 35 ml |
| Benzyl Alcohol NF* | 4.5 ml |
| Stock Solution ($CaCl_2$ 8 mM solution) | 415 ml |
| Tween 80** | 5.0 ml |

*Not to be added to the 2% minoxidil liposome formulation without preservatives.
* & **If Tween 80 and/or benzoyl alcohol are used they displace an equivalent volume of $CaCl_2$ solution.

2 g minoxidil and 25 mg BHA are dissolved in 50 ml ethanol in a 1 liter flask then add 35 ml propylene glycol and 4.5 ml benzoyl alcohol (if preservative is needed for the formulation). With continuous stirring, 415 ml ( )r 410.5 ml if preservative is used) $CaCl_2$ stock solutions gradually added.

The flask plus glass beads and the above solution is prewarmed to 50°–55° C. in an oven or water bath. The solution is quickly added to the flask containing the beads, and all ports are sealed with stoppers and immediately shaken by hand vigorously for one minute. An orbital, gyro shaker is attached and the unit is maintained in a controlled temperature environment (may be an oven) of 50°–55° C. and shaken for 20 min until a uniform "milky white" suspension of liposomes is obtained and all of the thin film of phospholipid has been removed from the inside of the flask and from the surface of the beads. The gyro shaker dial was set to 200 rpm. The 2L pear shaped flask is placed on the shaker at a 75° angle (approximately). This angle provides greater shaking effect as the beads swirling around the flask land covering most of the available space.

After one hour, the liposomes are formed and may be seen by examining a drop microscopically.

EXAMPLE 11

Comparison of Multiphase Liposomal Preparation, Suspension, and Solution Preparations of Minoxidil The minoxidil disposition of two liposomal formulations, prepared using Soy Phosphatide in place of dipalmitoyl phosphatidyl-choline, were tested against a suspension and a solution form. All preparations contained 2% minoxidil. The chemical composition of the liposomal and suspension forms were identical, except one liposomal product did not contain a preservative, benzyl alcohol.

| Formula for Products Tested. | |
|---|---|
| 1. Liposomal Minoxidil without Preservative | |
| 240 mg | Lecithin (Soy Phosphatide NC 95-H) |
| 120 mg | Cholesterol (USP) |
| 120 mg | Minoxidil Milled (600 Ci 3H) |
| 0.3 mg | Butylated Hydroxyanisole (USP) |
| 0.054 ml | Benzyl Alcohol NF |
| 0.6 ml | Ethanol 95% (USP) |
| 0.42 ml | Propylene Glycol (USP) |
| 4.926 ml | $CaCl_2$ (8 mM) solution |
| 2. Liposomal Minoxidil with Preservative | |
| 240 mg | Lecithin (Soy Phosphatide NC 95-H) |
| 120 mg | Cholesterol (USP) |
| 120 mg | Minoxidil Milled (600 Ci 3H) |
| 0.3 mg | Butylated Hydroxyanisole (USP) |
| 0.6 ml | Ethanol (95%), (USP) |
| 0.42 ml | Propylene Glycol (USP) |
| 4.98 ml | 8 mM $CaCl_2$ Solution |
| 3. Minoxidil Suspension | |
| 240 mg | Lecithin (Soy Phosphatide NC 95-H) |
| 120 mg | Cholesterol (USP) |
| 120 mg | Minoxidil Milled (600 Ci 3H) |
| 0.3 mg | Butylated Hydroxyanisole (USP) |
| 0.054 ml | Benzyl Alcohol NF |
| 0.552 ml | Ethanol (95%), (USP) |
| 0.384 ml | Propylene Glycol (USP) |
| 4.56 ml | 8 mM $CaCl_2$ Solution |
| 4. Minoxidil Solution | |
| 120 mg | Minoxidil Milled (600 Ci 3H) |
| 3.6 ml | Ethanol (95%), (USP) |
| 1.2 ml | Propylene Glycol (USP) |
| 1.2 ml | Distilled Water |
| 4.98 ml | 8 mM $CaCl_2$ Solution |

The liposomal products were prepared as described in Example 10, "scaled down" to make 6.0 ml batches.

The suspension was prepared by first blending the solids through a conventional sieving process. The solids are stirred into the liquid components, and the mixture is maintained at room temperature. Analysis of the suspension indicates virtually no liposomes are formed. The solution was prepared by conventional means.

Four groups of guinea pigs (control and test groups) were used. Each group contained seven guinea pigs weighing 250–350 g, housed in individual cages. The hair of the dorsal area was clipped off and an area of 3×3 cm was marked. In place of the previous dose of 0.1 ml here the dose was only 0.05 ml. The 0.05 ml dose of the control or test preparation was applied in a "twice a day" dosage schedule, i.e., t=0, 8, 24, 32, 48, 56 and 72 hr.

Four hours after the last treatment the guinea pigs were killed under $CO_2$ atmosphere; blood and other tissue samples were taken immediately. Before the skin was dissected the treated area was washed with guaze swabs soaked in ethanol to remove product that remained on the surface of the skin. The samples were kept in deep freeze ($-16°$) condition until processed for radioactivity analysis. Before slicing the skin samples, the hair grown during the four day-treatment was shaved off and added to the swab fraction. The combined hair and swab should contain minoxidil remaining on the surface of the skin. The skin samples were sliced horizontally with a Castroviejo Keratotome, set at 0.2 mm slice which was designated as the epidermis, then 0.5 mm slice which was referred to as dermis and the remaining portion labelled as the subcutaneous tissue. The results are presented in the Tables and Figures attached.

In this study, one of the controls, the suspension preparation, contained the same chemical composition as the liposomal (MCL) products; the only difference in this control and the test preparations was that the minoxidil was present in the control preparation in "free" form, while in the test product the drug was mainly in the liposome-encapsulated form. The other control preparation was the solution form, which is an Upjohn formula.

The results are depicted in Tables V and VI. They clearly demonstrate that the liposomal encapsulation is responsible for the favorable drug disposition; i.e. an increased drug concentration in the skin.

TABLE I

| Method of Preparation | Percent of Minoxidil in the Final Liposomal Preparation |
|---|---|
| Multilamellar lipid vesicles (MLV) (Bangham, et al., J. Mol..Biol. 13:238–252, 1965) | 0.15% |
| Large Unilamellar vesicles (REV) (Szoka, et al., Proc. Natl. Acad. Sci. (USA) 75:4194–4198, 1978) | 0.2% |
| Multilamellar lipid vesicles (MLV) (U.S. Pat. No. 4,485,054) | 0.4% |

TABLE II

The Effect of Liposomal Encapsulation on Drug Disposition*
μg Minoxidil/g Tissue

| Tissue | Control Solution | | Liposome of Example 1 | | Liposome of Example 2 (Gel) | |
|---|---|---|---|---|---|---|
| | Mean | ± SD | Mean | ± SD | Mean | ± SD |
| Skin Surface | 3146.9 | 721.8 | 2411.2 | 327.9 | 3407.9 | 721.9 |

TABLE II-continued

The Effect of Liposomal Encapsulation on Drug Disposition*
μg Minoxidil/g Tissue

| Tissue | Control Solution Mean | ± SD | Liposome of Example 1 Mean | ± SD | Liposome of Example 2 (Gel) Mean | ± SD |
|---|---|---|---|---|---|---|
| Epidermis | 2886.3 | 219.6 | 13411.7* | 2270.9 | 11669.7* | 2302.2 |
| Dermis | 194.7 | 54.7 | 877.1* | 84.9 | 886.9* | 402.7 |
| Sub. Cut. | 25.8 | 10.3 | 267.3 | 157.8 | 146.4* | 64.8 |
| Brain | 0.458 | 0.174 | 0.281 | 0.132 | 1.47 | 0.59 |
| Heart | 1.884 | 0.779 | 1.608 | 0.213 | 3.19 | 1.01 |
| Kidney | 0.707 | 0.167 | 0.837 | 0.841 | 2.63* | 0.76 |
| Liver | 0.988 | 0.269 | 0.755 | 0.363 | 3.66* | 1.68 |
| Lung | 1.774 | 0.271 | 1.757 | 0.275 | 3.28** | 1.03 |
| Spleen | 1.425 | 0.607 | 1.305 | 0.198 | 3.10** | 0.87 |
| Urine[xx] | 379.03 | 315.05 | 55.53 | 48.78 | | |
| Blood | 0.0239 | 0.0090 | 0.0438 | 0.0360 | 0.120 | 0.094 |

*Seven doses of 0.1 ml preparation were applied on a 3 × 3 cm area (t = 0, 8, 24, 32, 48, 56, 72 hr).
The guinea pigs were sacrificed under $CO_2$ atmosphere four hours after last treatment.
[xx]Total urine, collected during the treatment period.
SD = Standard Deviation with N = 5
The degree of significance
*p < .005
**p < .05

TABLE III

The Effect of Liposomal Encapsulation on Drug Disposition*
μg Minoxidil/g Tissue

| Tissue | Control Mean | ± SD | Liposomal Gel 3% Mean | 3% ± SD |
|---|---|---|---|---|
| Skin Surface | 7999.3 | 2181.4 | 8164.4 | 2935.9 |
| Epidermis | 5116.3 | 1283.6 | 20758.0 | 6212.4 |
| Dermis | 312.1 | 43.2 | 1503.0 | 619.3 |
| Sub. Cut. | 95.1 | 31.7 | 519.1 | 256.6 |
| Brain | 2.39 | 0.81 | 5.32 | 2.69 |
| Heart | 2.51 | 1.39 | 8.99 | 2.69 |
| Kidney | 5.20 | 2.29 | 6.79 | 1.916 |
| Liver | 8.00 | 1.56 | 10.61 | 3.88 |
| Lung | 4.37 | 1.06 | 9.67 | 2.44 |
| Spleen | 5.11 | 0.76 | 9.99 | 2.55 |
| Urine** | 8255.3 | 1084.7 | | |
| Blood | 0.0563 | 0.0389 | | |

*Seven doses of 0.1 ml preparation were applied on a 3 × 3 cm area (t = 0, 8, 24, 32, 48, 56, 72 hr). The guinea pigs were sacrificed under $CO_2$ atmosphere four hours after last treatment.
**Total urine, collected during the treatment period.

TABLE VA

The Effect of Dosage Form on Drug Disposition
μg Minoxidil/g Tissue

| Tissue | Liposomes (with preservative) Mean | ± SD | Liposomes (without preservative) Mean | ± SD |
|---|---|---|---|---|
| Epidermis | 4350.3 | 2903.9 | 4186.8 | 2824.7 |
| Dermis | *524.8 | 298.6 | **343.3 | 108.2 |
| Sub. Cut. | **80.1 | 34.6 | **90.2 | 26.8 |
| Skin Surface | 292921.4 | 79447.8 | 165071.4 | 54371.5 |
| Blood | 0.017 | 0.013 | 0.021 | 0.006 |
| Brain | 0.444 | 0.133 | 0.510 | 0.172 |
| Liver | 0.976 | 0.436 | *1.234 | 0.392 |
| Spleen | *0.701 | 0.143 | 0.612 | 0.129 |
| Kidney | 0.676 | 0.235 | *0.849 | 0.152 |
| Lung | *0.668 | 0.086 | *0.624 | 0.091 |
| Heart | *0.673 | 0.120 | 0.568 | 0.138 |
| Urine | *626.5 | 223.4 | | |

Seven doses of 0.05 ml preparation were applied on a 3 × 3 cm area (t = 0, 8, 24, 32, 48, 56, 72 hr). The guinea pigs were sacrificed under $CO_2$ atmosphere four hours after the last treatment.
Total urine, collected during the treatment period.
SD = Standard Deviation with N = 7. The degree of significance
*p < 0.01
**p < 0.001

TABLE IV

The Effect of Liposomal Encapsulating on Drug Disposition After 72 Hour-Treatments[a]
μg Econazole-$NO_3$/g Tissue

| Tissue | Pevaryl Control Cream Mean | ± SD[b] | Liposomes Example 7 Mean | ± SD | Liposomes Example 8 Mean | ± SD |
|---|---|---|---|---|---|---|
| Epidermis | 832.5 | 311.0 | 7311.9 | 2644.4 | 6379.2 | 3823.8 |
| Dermis | 138.7 | 53.1 | 270.9 | 105.0 | 226.9 | 59.3 |
| Sub. Cut. | 20.0 | 15.0 | 50.7 | 29.9 | 24.0 | 21.0 |
| Skin Surface | 703.2 | 151.6 | 3028.1 | 2317.9 | 1111.9 | 178.9 |
| Blood | 0.166 | 0.045 | 0.213 | 0.173 | 0.022 | 0.004 |
| Brain | 0.345 | 0.063 | 0.445 | 0.312 | 0.469 | 0.138 |
| Liver | 5.832 | 1.145 | 6.63 | 2.41 | 0.101 | 0.003 |
| Spleen | 1.864 | 2.255 | 1.90 | 1.25 | 0.167 | 0.012 |
| Kidney | 2.158 | 0.501 | 5.10 | 3.98 | 0.220 | 0.032 |
| Lung | 1.465 | 0.148 | 3.40 | 2.71 | 0.036 | 0.013 |
| Heart | 0.522 | 0.177 | 1.81 | 1.41 | N.A. | N.A. |

[a]Seven doses of 0.1 ml preparation were applied on a 3 × 3 cm area (t = 0, 8, 24, 32, 48, 56, 72 hr). The guinea pigs were killed under $CO_2$ atmosphere 90 minutes after the last treatment.
[b]Standard Deviation; N = 5

TABLE VB

The Effect of Dosage Form on Drug Disposition

μg Minoxidil/g Tissue

| Tissue | Suspension Mean | ± SD | Solution Control Mean | ± SD |
|---|---|---|---|---|
| Epidermis | 1958.7 | 879.4 | 1291.4 | 304.3 |
| Dermis | 139.8 | 82.1 | 108.9 | 52.3 |
| Sub. Cut. Skin | 29.9 | 17.5 | 16.2 | 4.1 |
| Surface | 78300.7 | 56009.0 | 84804.7 | 33091.1 |
| Blood | 0.031 | 0.027 | 0.008 | 0.005 |
| Brain | 0.618 | 0.236 | 0.301 | 0.125 |
| Liver | *1.275 | 0.260 | 0.695 | 0.137 |
| Spleen | *0.804 | 0.216 | 0.417 | 0.072 |
| Kidney | 0.927 | 0.244 | 0.515 | 0.159 |
| Lung | *0.872 | 0.285 | 0.404 | 0.089 |
| Heart | *0.749 | 0.198 | 0.394 | 0.077 |
| Urine | *954.1 | 264.7 | 1554.4 | 278.9 |

Seven doses of 0.05 ml preparation were applied on a 3 × 3 cm area (t = 0, 8, 24, 32, 48, 56, 72 hr). The guinea pigs were sacrificed under $CO_2$ atmosphere four hours after the last treatment.

Total urine, collected during the treatment period.

SD = Standard Deviation with N = 7.

The degree of significance

*$p < 0.01$

**$p < 0.001$

TABLE VI

Changes in Minoxidil Concentration due to Liposome-Encapsulation Expressed as Percent of Control

| Tissue | % of Control (suspension) Liposomes (with preservative) | Liposomes (without preservative) | % of Control (solution) Liposomes (with preservative) | Liposomes (without preservative) |
|---|---|---|---|---|
| Epidermis | 222.1 | 213.7 | 345.4 | 194.6 |
| Dermis | 375.4 | 245.5 | 481.9 | 315.2 |
| Sub. Cut. Skin | 267.9 | 3-1.7 | 494.4 | 556.8 |
| Surface | 374.1 | 210.8 | 345.4 | 194.6 |
| Blood | 54.8 | 67.7 | 212.5 | 266.2 |
| Brain | 71.8 | 82.5 | 147.5 | 169.4 |
| Liver | 76.5 | 96.3 | 140.4 | 177.5 |
| Spleen | 87.2 | 76.1 | 168.1 | 146.7 |
| Kidney | 72.9 | 91.6 | 131.3 | 164.8 |
| Lung | 76.6 | 71.5 | 165.3 | 154.4 |
| Heart | 89.8 | 75.8 | 170.8 | 144.2 |
| Urine | 65.7 | | 40.3 | |

We claim:

1. A method for administering a slightly water soluble biologically active compound comprising:
   topically applying a pharmaceutical composition comprising:
   (a) multilamellar lipid vesicles with a slightly water soluble biologically active compound captured therein;
   (b) a saturated solution of the biologically active compound; and
   (c) the biologically active compound in solid form.

2. A method of claim 1, wherein the compound is minoxidil.

3. A method of claim 1, wherein the compound is econazole nitrate or econazole base.

4. A method of claim 1, wherein the composition is dispersed in a hydrocolloid gel.

5. A method of claim 4, wherein the compound is minoxidil.

6. A method of claim 4, wherein the compound is econazole nitrate or econazole base.

* * * * *